(12) United States Patent
Poncon

(10) Patent No.: US 9,308,317 B2
(45) Date of Patent: Apr. 12, 2016

(54) DRUG DELIVERY DEVICE AND ADAPTOR

(75) Inventor: Gilbert Poncon, Pommiers la Placette (FR)

(73) Assignee: Becton Dickinson France, Le Pont-de-Claix (FR)

( * ) Notice: Subject to any disclaimer, the term of this patent is extended or adjusted under 35 U.S.C. 154(b) by 81 days.

(21) Appl. No.: 14/232,760

(22) PCT Filed: Jul. 13, 2012

(86) PCT No.: PCT/EP2012/063829
§ 371 (c)(1),
(2), (4) Date: Jan. 14, 2014

(87) PCT Pub. No.: WO2013/010953
PCT Pub. Date: Jan. 24, 2013

(65) Prior Publication Data
US 2014/0142553 A1   May 22, 2014

(30) Foreign Application Priority Data
Jul. 15, 2011   (EP) ..................................... 11305928

(51) Int. Cl.
| A61M 25/16 | (2006.01) |
| A61M 25/18 | (2006.01) |
| A61M 39/00 | (2006.01) |
| A61M 39/10 | (2006.01) |
| A61M 5/14 | (2006.01) |
| A61M 5/34 | (2006.01) |

(52) U.S. Cl.
CPC ............. *A61M 5/1413* (2013.01); *A61M 5/345* (2013.01); *A61M 39/1011* (2013.01); *A61M 2039/1027* (2013.01); *A61M 2039/1033* (2013.01); *A61M 2039/1077* (2013.01)

(58) Field of Classification Search
CPC ............... A61M 2025/024; A61M 2025/0253; A61M 2025/026; A61M 2025/028; A61M 25/02
See application file for complete search history.

(56) References Cited

U.S. PATENT DOCUMENTS

| 4,895,570 A | 1/1990 | Larkin |
| 5,342,322 A * | 8/1994 | Nathan et al. ................. 604/192 |
| 5,925,032 A * | 7/1999 | Clements .......................... 606/1 |
| 2005/0065481 A1 | 3/2005 | Hauri et al. |

FOREIGN PATENT DOCUMENTS

GB   2240477 A   8/1991

* cited by examiner

*Primary Examiner* — Rebecca E Eisenberg
(74) *Attorney, Agent, or Firm* — The Webb Law Firm

(57) ABSTRACT

Provided herein is a drug delivery device including: a reservoir for a product, said reservoir having a distally projecting end-piece defining an axial passageway for the transfer of the product, said end-piece having a distal portion, an adaptor having a collar engageable around said end-piece, and a securing structure for locking the axial movement of said collar with respect to said end-piece. The adaptor further comprises a foldable element capable of going from a folded configuration in which said foldable element substantially surrounds said distal portion of said end-piece, to an unfolded configuration, in which said foldable element leaves said distal portion uncovered. An adaptor for forming a drug delivery device is also provided.

16 Claims, 5 Drawing Sheets

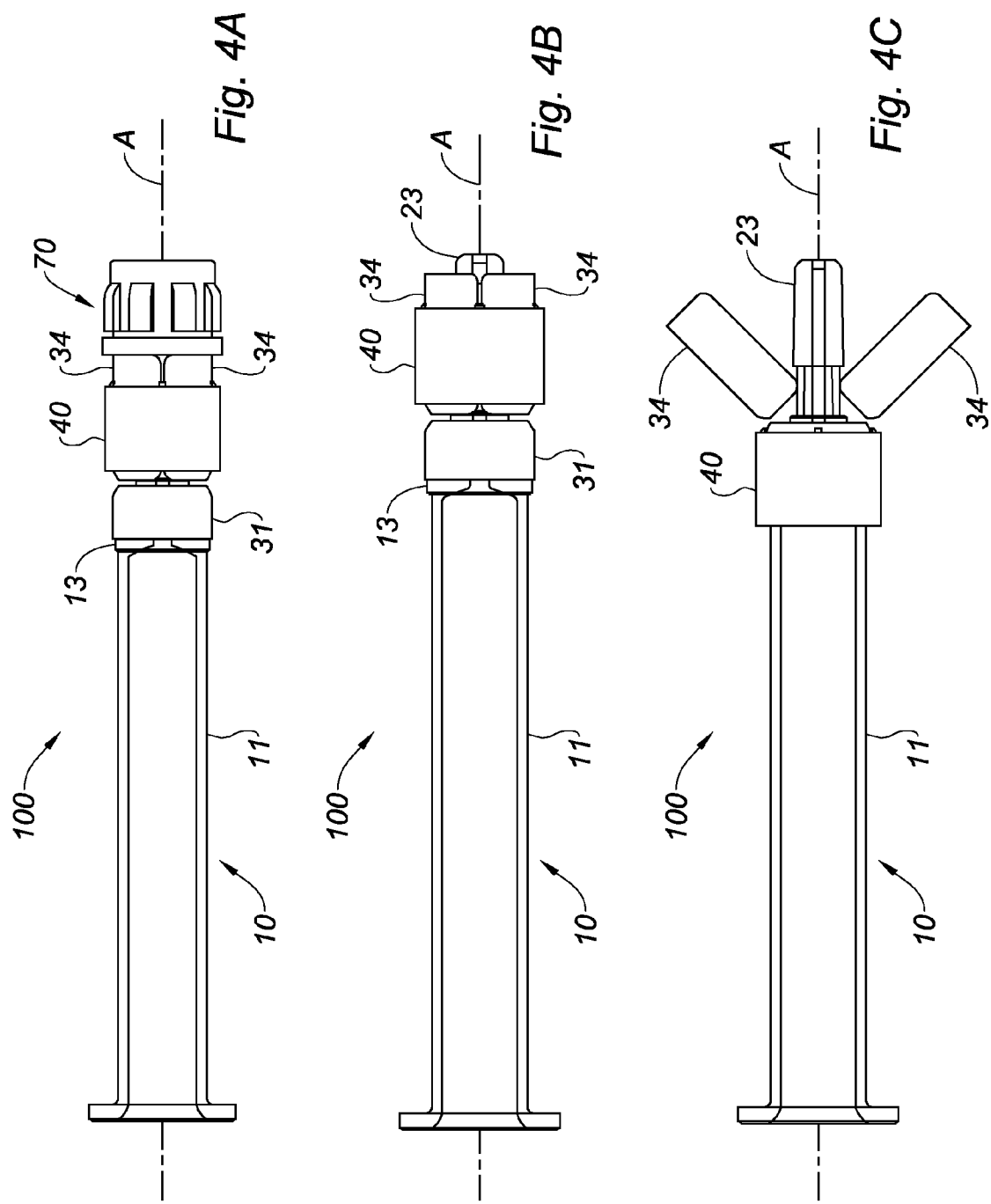

DRUG DELIVERY DEVICE AND ADAPTOR

BACKGROUND OF THE INVENTION

1. Field of the Invention

The present invention relates to a drug delivery device and an adaptor for, or intended to be used with said drug delivery device. The drug delivery device is provided with an end-piece around which the adaptor is engageable so as to enable the safe connection of a connector on said end-piece.

2. Description of the Related Art

Drug delivery devices usually comprise a hollow body forming a reservoir for containing a medical product. In addition, the distal end of the body forming the reservoir usually comprises an end-piece in which an axial passageway is arranged through which the said product is ejected from the reservoir.

In this disclosure, the distal end of a component or of a device must be understood as meaning the end furthest from the hand of the user and the proximal end must be understood as meaning the end closest to the hand of the user. Similarly, in this disclosure, the distal direction must be understood as the direction of injection or transfer of the product (i.e. from the reservoir to the Intra Veinous line) and the proximal direction is the opposite direction.

The handling of products, such as liquid medicine, in particular for a parenteral administration to a patient which is carried out via a perfusion device implies, in a general manner, the use of connectors, such as IV (Intra Veinous) connectors which link the drug delivery device, containing the product to be delivered, to the vein of the patient, usually via an IV line. Of course, the drug delivery device, in particular its end-piece and the connector must be assembled together correctly and securely.

Actually, there are different connection systems for connecting a connector to the end-piece of a drug delivery device, when the distal portion of said end-piece has the global shape of a distally tapered cone, also called a male luer, as is usually the case.

In such cases, the male luer of the end-piece forming the male part of the connection system, the connector usually comprises a corresponding conical bore forming the female part of the connection system, also called a female luer, and intended to be fitted on the male luer in order to complete the connection.

In some cases, no additional element is provided on the connector, and the female luer is directly fitted on the male luer of the end-piece of the drug delivery device by simple force fitting: the connector is then called a luer slip connector and the connection is called a luer slip connection.

Alternatively, the connection system may comprise in addition an adaptor, said adaptor being fixed to the end-piece of the drug delivery device via a collar, and comprising a tubular wall at least partially surrounding the male luer of the end-piece. The tubular wall is provided with an inner thread intended to cooperate with a corresponding outer thread located on an outer wall of the connector provided with the female luer. In such a case, at the time of forming the connection, the female luer is fitted onto the male luer by means of threading the connector in the adaptor: the safe connection of the male luer and female luer is therefore improved. Such an adaptor is called a luer Lock Adaptor, the connector is called a luer Lock connector and the connection thus realized is called a luer lock connection. Alternatively, the threads may be replaced by cooperating wings.

It derives from these two connection systems that all the connectors may not have the same shapes: the connectors to be used for a luer Lock connection will comprise an outer thread (or a wing), whereas the connectors to be used for a luer slip connection will not. Indeed, if a luer slip connector is brought close to the distal portion of the end-piece of a drug delivery device provided with a luer Lock adaptor as described above, the luer Lock adaptor will be an obstacle to the female luer of the luer slip connector and will prevent the completion of a safe connection between the drug delivery device and the connector.

SUMMARY OF THE INVENTION

One aspect of the invention is to provide an adaptor engageable with the end-piece of a drug delivery device, in particular where the end-piece has a distal portion having a distally tapered cone shape such as a male luer, said adaptor being capable of easily changing configurations so as to allow both types of connections, luer slip and luer lock, as described above, depending on which type of connector is provided, with no particular effort from the user. In particular, one aspect of the invention is to provide an adaptor engageable on the end-piece of a drug delivery device and allowing successive connections of various connector types, in particular luer lock and luer slip types, with no need for the user to reconfigure the drug delivery device between two connections, regardless of the type of the selected connector.

A first aspect of the invention is a drug delivery device comprising:

a reservoir for containing a product, said reservoir having a distally projecting end-piece having a longitudinal axis A and defining an axial passageway for the transfer of the product from the reservoir, said end-piece having a distal portion, an adaptor having a collar engageable around said end-piece, securing means for locking the axial movement of said collar with respect to said end-piece once said collar is engaged around said end-piece, wherein said adaptor further comprises a foldable element capable of going from a folded configuration in which said foldable element substantially surrounds said distal portion of said end-piece, and an unfolded configuration, in which said foldable element leaves said distal portion at least partially uncovered.

In particular, as will appear from the description below, in its unfolded configuration, the foldable element leaves a significant part of said distal portion uncovered, so that a luer slip connector may be connected on said uncovered significant part of said distal portion.

As will be clear from the following description, the adaptor of the drug delivery device of the invention is capable of easily changing configurations for allowing either a luer slip connection to be completed, or a luer lock connection to be completed. Indeed, when the foldable element of the adaptor is in its folded configuration, a luer slip connector can be easily fitted on said distal portion, the adaptor forming no obstacle to this connection: the user needs only apply a proximal pressure to the foldable element, for example simply via the luer slip connector, so as to cause the foldable element to unfold, in order to connect the luer slip connector onto the distal portion of the end-piece.

Alternatively, if the user wishes to connect a luer Lock connector to the end-piece, the user does not need to apply a proximal pressure on the adaptor to unfold the foldable element. The luer lock connection can therefore be completed by simply connecting the luer Lock connector to the adaptor, for example by threading, thereby completing a safe connection between the female luer and the distal portion of the end-piece.

In embodiments, the drug delivery device further comprises releasable locking means for releasably maintaining said foldable element in its folded configuration.

In embodiments, said foldable element comprises two semi tubes extending from the collar, said two semi tubes merging so as to form a single tube extending from the collar in the distal direction, in the folded configuration of said foldable element, the two semi tubes extending from the collar outwardly in opposite transverse directions when said foldable element is in its unfolded configuration.

In embodiments, said releasable locking means comprise a ring capable of receiving at least partially said adaptor, said ring being axially movable with respect to said adaptor, between a locking position, in which said ring surrounds said single tube formed by said two semi tubes in the folded configuration of said foldable element, thereby preventing said two semi tubes to extend outwardly in opposite transverse directions, and a free position, in which said ring does not surround said semi tubes, thereby allowing said two semi tubes extending from the collar outwardly in opposite transverse directions.

For example, said ring may be force fitted around the adaptor.

In embodiments, said ring further comprises at least a leg extending in the distal direction, the distal end of said leg extending beyond a distal end of said distal portion, when said ring is in its locking position. Such an embodiment allows an automatic proximal movement of the ring for freeing the foldable element, when the user draws a luer slip connector close to the distal end of the distal portion of the end-piece. By entering in contact with the distal end of the leg, the luer slip pushes said leg in the proximal direction, thereby causing the proximal movement of the ring in the proximal direction, and allowing the foldable element, in other words the two semi tubes, to unfold.

In embodiments, in a storage position of the drug delivery device, the ring may be linked to the adaptor by breakable bridges. In such embodiments, the user breaks the breakable bridges in order to be able to move the ring from its locking position to its free position and vice-versa.

In embodiments, the inner walls of said semi tubes are provided with portions of thread forming a continuous thread when the foldable element is in its folded configuration and said semi tubes form a single tube. The continuous thread is intended to cooperate with the outer thread of a luer Lock connector at the time a luer Lock connector is connected onto the end-piece.

In embodiments, the drug delivery device comprises anti-rotation means for limiting the rotation of said collar with respect to the end-piece once said collar is engaged with said end-piece. Said anti-rotation means may comprise one or more longitudinal ridge(s) located on an outer wall of said end-piece, and one or more recess(es) located on an inner wall of said collar, said longitudinal ridge being engaged into said recess and thereby preventing said collar to rotate with respect to said end-piece. Such anti-rotation means allow a safe threading of the luer Lock connector into the adaptor, as the adaptor is maintained locked in rotation with respect to the end-piece when the luer Lock connector is threaded therein.

In embodiments, said end-piece is made of glass. Alternatively, said end-piece may be made of plastic.

In embodiments, said distal portion is a male luer, in other words is a distally tapered cone.

In embodiments, said securing means comprise a transversal wall of said reservoir, and an annular ridge provided on an outer wall of said end-piece, said collar being in proximal abutment against said transversal wall and in distal abutment against said annular ridge once it is engaged around said end-piece. For example, the securing means further comprise flexible tabs located on an inner wall of said collar, said flexible tabs being in proximal abutment against said transversal wall and in distal abutment against said annular ridge once said collar is engaged around said end-piece.

Another aspect of the present invention is an adaptor as described above, arranged for cooperating with a reservoir having a distally projecting end-piece having a longitudinal axis and defining an axial passageway for the transfer of the product from the reservoir, for forming a drug delivery device as described herein, said adaptor having a collar engageable around said end-piece, said adaptor further comprising a foldable element capable of going from a folded configuration in which said foldable element substantially surrounds a distal portion of said end-piece, and an unfolded configuration, in which said foldable element leaves said distal portion at least partially uncovered.

BRIEF DESCRIPTION OF THE DRAWINGS

The drug delivery device and adaptor of the invention will now be further described in reference to the following description and attached drawings in which:

FIGS. 4A to 4C are side views of the drug delivery device of FIG. 1 in a storage position, in a luer lock connection position, and in a luer slip connection position.

DETAILED DESCRIPTION

Figure 1:
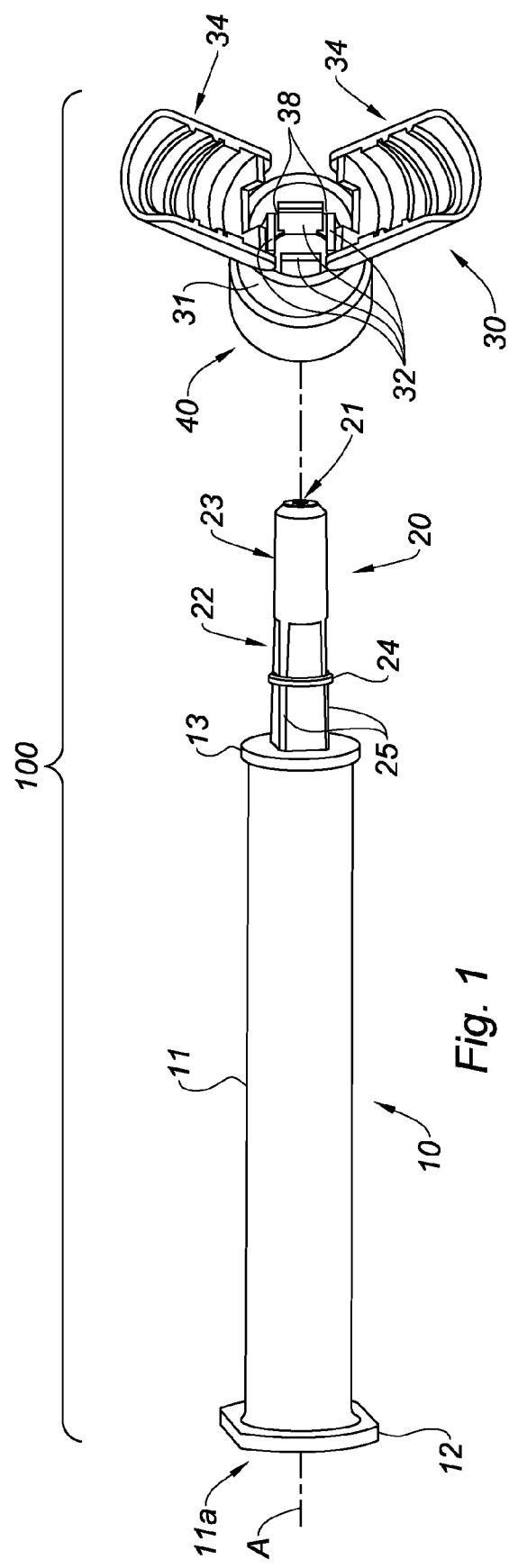
FIG. 1 is a perspective view of a drug delivery device of the invention, before engagement of the adaptor onto the end-piece of the drug delivery device.

With reference to FIG. 1 is shown a drug delivery device 100 of the invention comprising a reservoir 10 having a distally projecting end-piece 20 and an adaptor 30 intended to be engaged onto the end-piece 20. As appears from this Figure, all the elements of the drug delivery device 100, in other words the reservoir 10, the end-piece 20 and the adaptor 30, are aligned along a longitudinal axis A.

The reservoir 10 is intended to contain a product to be delivered to a patient. The reservoir 10 may be formed of any material suitable for storing a product such as a medicine or drug. It may be made out of glass or plastic materials. On the example shown, the reservoir 10 has the global shape of a syringe body and comprises a tubular barrel 11, open at its proximal end 11a where it is provided with an outer flange 12 intended to form a pushing surface for the user at the time of delivery of the product to a patient.

At its distal end, the tubular barrel 11 is substantially closed by a transversal wall 13, except for a central opening 14 (see FIG. 5A) for the passage of the product towards the end-piece 20.

Figure 5A:
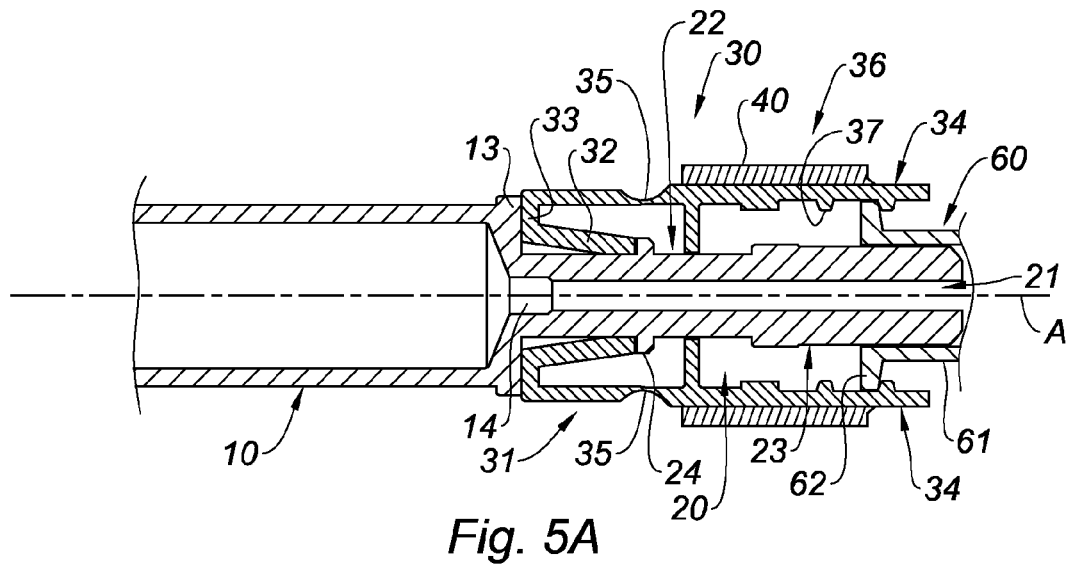
FIGS. 5A and 5B are partial cross section views of the drug delivery device of FIG. 1 in a luer Lock position and in a luer slip position.
Figure 5B:
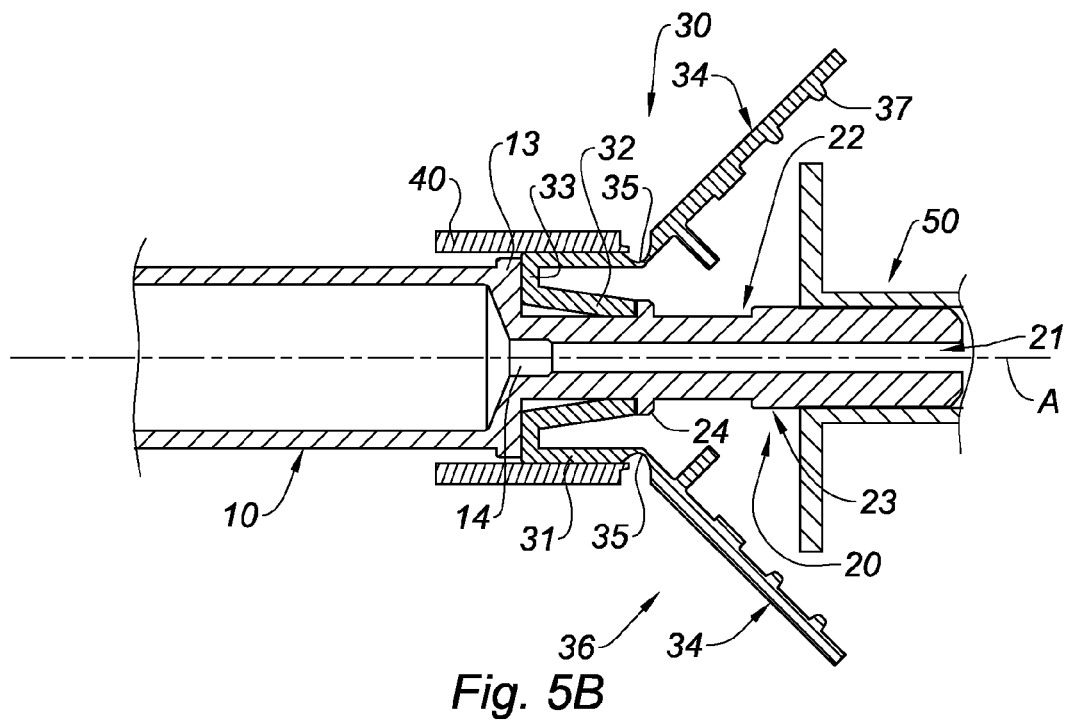

With reference to FIGS. 1 and 5B-C, the reservoir 10 is further provided with a distally projecting end-piece 20, extending from the transversal wall 13, aligned on longitudinal axis A and defining an axial passageway 21 (see FIGS. 5A and 5B) for the transfer of the product (not shown) from the reservoir 10 to the outside, in particular to a connector (partially shown on FIGS. 5A and 5B).

With reference to FIGS. 1 and 5A and 5B, the end-piece 20 is provided with a proximal portion 22, extending distally from the transversal wall 13 and having a tubular shape showing a constant outer diameter. The end-piece 20 is further provided with a distal portion 23, extending from the distal end of the proximal portion 22, and having a distally tapered conical shape, also called a male luer. The outer wall of the proximal portion 22 is further provided with an annular ridge 24.

As appears from FIG. 1, the proximal portion 22 of the end-piece 20 is further provided on its outer wall with four (only two are visible on FIG. 1) longitudinal ridges 25 regularly distributed along a circumference of the proximal portion 22.

With reference to FIGS. 1-3 and 5A-5B, the adaptor 30 will now be described in detail. The adaptor 30 comprises a collar 31 capable of being engaged around, and in contact with, the outer wall of the end-piece 20. The collar 31 comprises on its inner wall an annular transversal wall 33 provided with radial flexible tabs 32 capable of outwardly deflecting when the collar 31 is mounted on the distal portion 23 of the end-piece 20 and of coming back to their rest state, as shown on FIGS. 2, 5A and 5B, once the collar 31 is engaged around the proximal portion 22 of the end-piece 20. In its position where it is engaged around the proximal portion 22 of the end-piece 20, as shown on FIGS. 5A and 5B, the flexible tabs 32 of the collar 31 are in proximal abutment against the transversal wall 13 of the reservoir 10 and in distal abutment against the annular ridge 24 of the proximal portion 22. The transversal wall 13 and the annular ridge 24 therefore form securing means for locking the axial movement of the collar 31 with respect to the end-piece 20 once the collar 31 is engaged around the end-piece 20. On the example shown, the collar 31 has four radial flexible tabs 32, regularly distributed along the circumference of the collar 31. The interspaces between these four radial flexible tabs 32 define four radial recesses 38.

Figure 2:
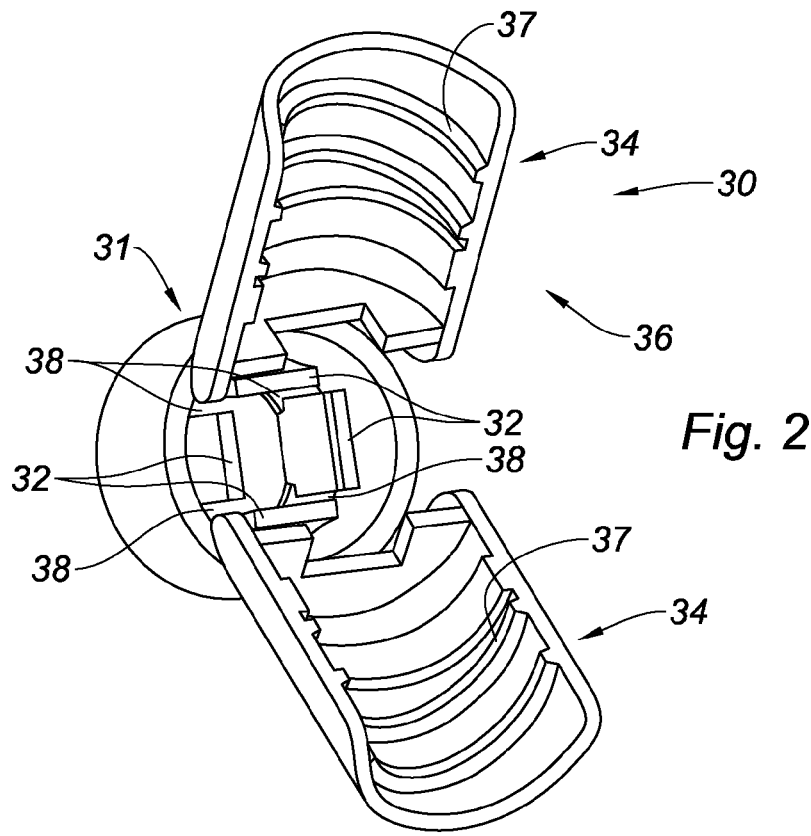
FIG. 2 is a perspective view of the adaptor of FIG. 1 in an unfolded configuration.

With reference to FIGS. 2 and 5A and 5B, the adaptor 30 is further provided with two semi tubes 34, extending from the collar 31 in the distal direction, and linked to the collar 31 by means of hinges 35. The two semi tubes 34 and the hinges 35 form altogether a foldable element 36 capable of going from a folded configuration, as shown on FIG. 5A, in which the foldable element 36 substantially surrounds the distal portion 23 of the end-piece 20, to an unfolded configuration, as shown in FIG. 5B, in which the foldable element 36 leaves a significant part of the distal portion 23 of the end-piece uncovered.

On the example shown, the foldable element 36 is made of the two semi tubes 34 and the hinges 35: as such, in the folded configuration of the foldable element 36, the two semi tubes 34 merge together so as to form a single tube surrounding substantially the distal portion 23 of the end-piece. On the contrary, in the unfolded configuration of the foldable element 36, the two semi tubes extend from the collar 31 outwardly in opposite transverse directions, as shown on FIGS. 2 and 5B.

In addition, the inner walls of the semi tubes 34 are provided with portions of thread forming a continuous thread 37 in the folded configuration of the foldable element 36, the function of which will be explained later.

The drug delivery device 100 further comprises a ring 40 capable of receiving at least partially the adaptor 30. As will appear form the description below, the ring 40 is axially movable with respect to said adaptor 30, when said adaptor is engaged around the end-piece 20. For example, the ring 40 may be force fitted around the adaptor 30, in particular around the collar 31.

Figure 3:
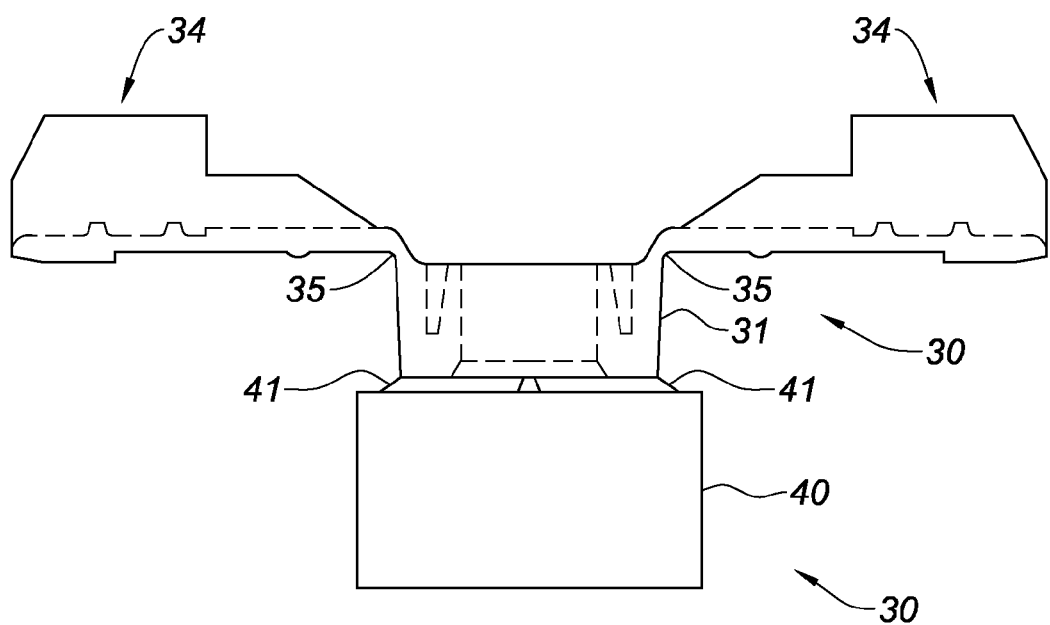
FIG. 3 is a side view of the adaptor of FIG. 1 in an unfolded configuration, with locking means attached thereto.

On FIG. 3 is shown the adaptor 30 and the ring 40 molded as a single element: the ring 40 is linked to the adaptor 30 via breakable bridges 41. This configuration of the ring 40 and the adaptor 30 corresponds to a storage position of the drug delivery device 100, before use of the adaptor 30. When the user wishes to use the adaptor 30, he simply breaks the breakable bridges 41 in order to be able to move the ring 40 axially.

The operation of the adaptor 30 and the drug delivery device 100 will now be explained with reference to FIGS. 1-5B.

The drug delivery device 100 may be provided with the adaptor 30 not yet engaged around the end-piece 20, and still linked to the ring 40 as shown on FIGS. 1 and 3. In order to be operational, the adaptor 30 is engaged onto the end-piece 20 of the reservoir 10. To this purpose, the proximal end of the adaptor 30, or of the ring 40 in case the ring 40 has not yet been detached from the adaptor 30, is approached from the distal end of the end-piece 20: thanks to the capability of the radial flexible tabs 32 to deflect outwardly, the collar 31 is force-fitted onto the distal portion 23 of the end-piece 20 and pushed in the proximal direction until it reaches the outer wall of the proximal portion 22, located between the transversal wall 13 of the reservoir 10 and the annular ridge 24, around which it is fitted: in this position of the adaptor 30, the radial flexible tabs 32 come back to their rest state and may be in contact with the outer wall of the proximal portion 22. As already mentioned, the collar 31 is engaged between the transversal wall 13 and the annular ridge 24 via its flexible tabs 32 and it is therefore locked in translation both in the distal and proximal directions.

The ring 40 may then be detached from the adaptor 30 by the user by simply breaking the breakable bridges 41: the ring 40 may then be moved axially by the user in the distal direction so as to surround the collar 31 as shown on FIG. 5B. For example, the ring 40 is force fitted around the collar 31 and it remains linked to the collar 31 by friction. Alternatively, in other embodiments, the ring may be placed in this position during the manufacturing of the product.

In the free position of the ring 40 as shown on FIG. 5B, the foldable element 36 is in an unfolded configuration, and the two semi tubes 34 extend from the collar 31 outwardly in opposite transverse directions, thereby leaving free a significant part of the distal portion 23 of the end-piece 20. The drug delivery device 100 is in a luer slip connection position, as shown on FIG. 4C, and a luer slip connector 50 (partially shown on FIG. 5B) may then be approached to the distal portion 23 of the end-piece, on which it can be easily fitted: indeed, in this unfolded configuration of the foldable element 36, the adaptor does not constitute an obstacle to the connection of the luer slip connector 50 to the end-piece 20, and the luer slip connector 50 can be connected onto the significant part of the distal portion 23 that is now left uncovered.

Alternatively, in case it is desired to connect a luer Lock connector to the end-piece, the ring 40 may be moved further distally by a user until it surrounds the two semi tubes 34, as shown on FIG. 5A: on this Figure, the two semi tubes 34 merge together so as to form a single tube and the foldable element 36 is in its folded configuration, in which it substantially surrounds the distal portion 23 of the end-piece 20. The ring 40 is therefore in a locking position. In this folded configuration of the foldable element 36, the portions of thread located on the inner walls of the semi tubes 34 form a continuous thread 37. The drug delivery device 100 is therefore in a luer Lock connection position, as shown on FIG. 4B and it is therefore possible to connect a luer Lock connector 60 (partially shown on FIG. 5A) provided with a female luer 61 and an outer thread 62 capable of cooperating with the thread 37 of the adaptor 30. The user has therefore no additional step to perform in order to complete a luer lock connection with a luer lock connector, other than threading the luer Lock connector 60 into the thread 37 of the adaptor 30: thanks to the four longitudinal ridges 25 of the proximal portion 22 being engaged in the four radial recesses 38 of the adaptor 30, and acting as anti-rotation means, the adaptor 30 remains locked in rotation with respect to the end-piece 20, when the luer Lock connector 60 is threaded thereon. The luer Lock connection is therefore safely completed.

As appears clearly from this description, the ring 40 forms releasable locking means for releasably maintaining the foldable element 36 in its folded configuration. As such, if it is desired to replace the luer Lock connector by a luer slip connector, the user may simply move the ring 40 back in the proximal direction and put it in its free position, in order to obtain a delivery device 100 in a luer slip connection position.

FIG. 4A shows the drug delivery device 100 of the invention, provided to the user with the adaptor 30 already engaged around the end-piece, the ring 40 being in its locking position, with a cap 70 closing the distal end of the drug delivery device 100. Once the cap 70 has been removed, the drug delivery device 100 may be used.

Figure 6A:
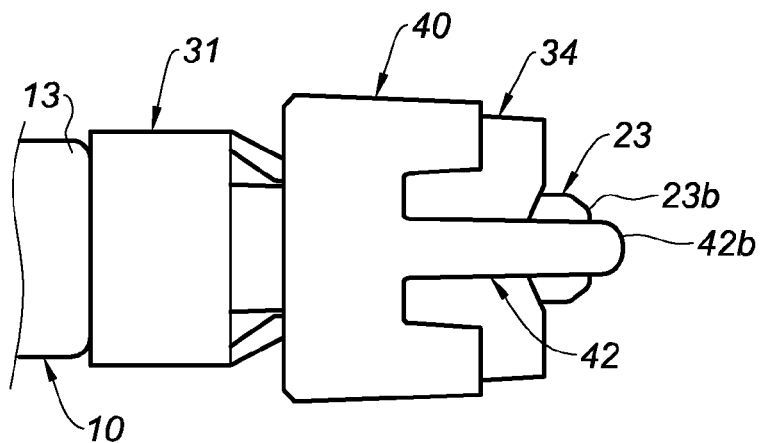
FIG. 6A is a partial side view of another embodiment of a drug delivery device of the invention in a luer Lock connection position.
Figure 6B:
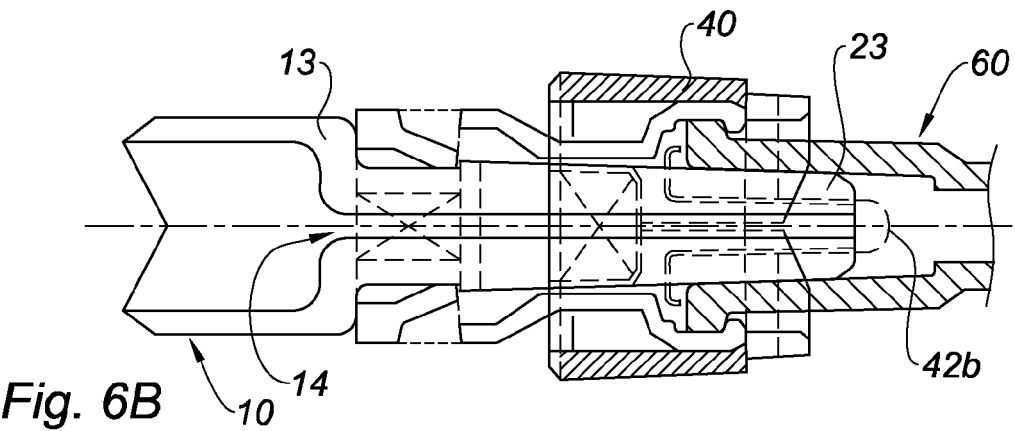
FIG. 6B is a partial cross section view of the drug delivery device of FIG. 6A showing partially the luer Lock connector.
Figure 6C:
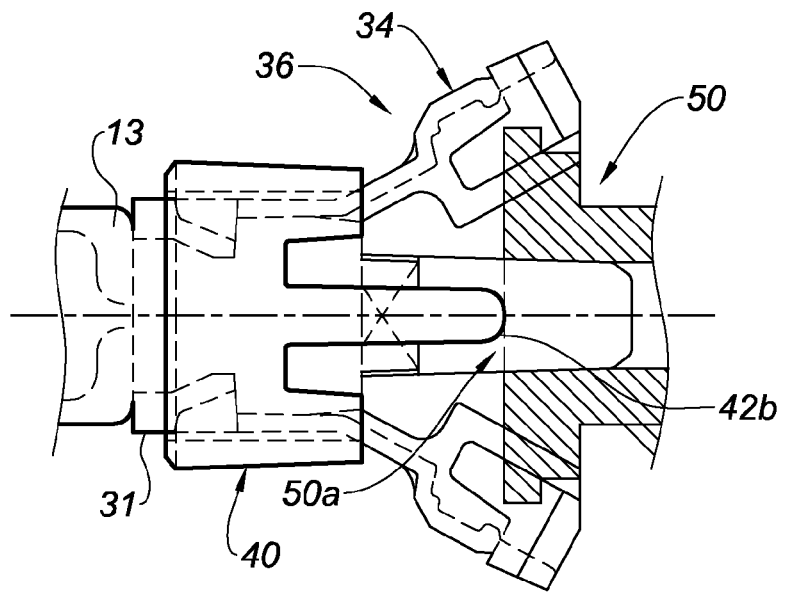
FIG. 6C is a partial side view of the drug delivery device of FIG. 6A in the luer slip connection position, showing partially the luer slip connector.

With reference to FIGS. 6A-6C, is shown another embodiment of the drug delivery device 100 of the invention, in which the ring 40 further comprises a leg 42 extending in the distal direction, the distal end 42b of said leg 42 extending beyond a distal end 23b of said distal portion 23, when the ring 40 is in its locking position, as shown on FIG. 6A. The references designating the same elements as in FIGS. 1-5B have been maintained.

As shown on FIG. 6B, the leg 42 does not constitute an obstacle to the connection of a luer lock connector 60 to the distal portion 23 of the end-piece 20 when the ring 40 is in its locking position.

With reference to FIG. 6C, when it is intended to connect a luer slip connector 50 to the distal portion 23 of the end-piece 20, the proximal end 50a of the luer slip connector 50 comes in contact with the distal end 42a of the leg 42 and it pushes the leg 42 proximally as the user approaches said luer slip connector 50 towards the distal portion 23 in order to connect it thereon. The ring 40 is therefore "automatically" pushed in the proximal direction and leaves its locking position towards its free position, thereby allowing the foldable element 36 to unfold and the semi tubes 34 to extend outwardly in opposite transverse directions: the distal portion 23 of the end-piece 20, at least a significant part of it, thus becomes uncovered and is ready to receive the female luer of the luer slip connector 50 to be fitted thereon.

The drug delivery device and adapter of the invention therefore allow changing connectors easily, quickly, between two successive connections, regardless of the type of connector that is used, in particular a luer lock connector or a luer slip connector.

The invention claimed is:

1. A drug delivery device comprising:
   a reservoir for containing a product, said reservoir having a distally projecting end-piece having a longitudinal axis A and defining an axial passageway for the transfer of the product from the reservoir, said end-piece having a distal portion,
   an adaptor having a collar engageable around said end-piece, and
   a securing structure for locking axial movement of said collar with respect to said end-piece once said collar is engaged around said end-piece, wherein
   said adaptor further comprises a foldable element capable of transitioning from a folded configuration in which said foldable element substantially surrounds said distal portion of said end-piece, to an unfolded configuration, in which said foldable element leaves said distal portion at least partially uncovered, the foldable element provided with threaded portions forming a continuous thread when the foldable element is in the folded configuration.

2. The drug delivery device according to claim 1, further comprising a releasable lock for releasably maintaining said foldable element in its folded configuration.

3. The drug delivery device according to claim 2, wherein said foldable element comprises two semi tubes extending from the collar, said two semi tubes merging so as to form a single tube extending from the collar in the distal direction, in the folded configuration of said foldable element, the two semi tubes extending from the collar outwardly in opposite transverse directions when said foldable element is in its unfolded configuration.

4. The drug delivery device according to claim 3, wherein said releasable lock comprises a ring capable of receiving at least partially said adaptor, said ring being axially movable with respect to said adaptor, between a locking position, in which said ring surrounds said single tube formed by said two semi tubes in the folded configuration of said foldable element, thereby preventing said two semi tubes to extend outwardly in opposite transverse directions, and a free position, in which said ring does not surround said semi tubes, thereby allowing said two semi tubes extending from the collar outwardly in opposite transverse directions.

5. The drug delivery device according to claim 4, wherein said ring further comprises at least a leg extending in the distal direction, a distal end of said leg extending beyond a distal end of said distal portion, when said ring is in its locking position.

6. The drug delivery device according to claim 4, wherein, in a storage position of said drug delivery device, said ring may be linked to said adaptor by breakable bridges.

7. The drug delivery device according to claim 3, wherein the inner walls of said semi tube are provided with the threaded portions forming the continuous thread when the foldable element is in its folded configuration and said semi tubes form a single tube.

8. The drug delivery device according to claim 1, further comprising an anti-rotation element for limiting rotation of said collar with respect to the end-piece once said collar is engaged with said end-piece.

9. The drug delivery device according to claim 8, wherein said anti-rotation means comprise one or more longitudinal ridges located on an outer wall of said end-piece, and one or more recesses located on an inner wall of said collar, said longitudinal ridges being engaged into said recesses and thereby preventing said collar to rotate with respect to said end-piece.

10. The drug delivery device according to claim 1, wherein said end-piece is made of glass.

11. The drug delivery device according to claim 1, wherein said end-piece is made of plastic.

12. The drug delivery device according to claim 1, wherein said distal portion is a male luer.

13. The drug delivery device-according to claim 1, wherein said securing structure comprises a transversal wall of said reservoir, and an annular ridge provided on an outer wall of said end-piece, said collar being in proximal abutment against said transversal wall and in distal abutment against said annular ridge once it is engaged around said end-piece.

14. The drug delivery device according to claim 13, wherein said securing structure further comprises flexible tabs located on an inner wall of said collar, said flexible tabs being in proximal abutment against said transversal wall and in, distal abutment against said annular ridge once said collar is engaged around said end-piece.

15. The drug delivery device according to claim 1, wherein said foldable element comprises two semi tubes extending from the collar, said two semi tubes merging so as to form a single tube extending from the collar in the distal direction, in the folded configuration of said foldable element, the two semi tubes extending from the collar outwardly in opposite transverse directions when said foldable element is in its unfolded configuration.

16. An adaptor arranged for cooperating with a reservoir having a distally projecting end-piece having a longitudinal axis A and defining an axial passageway for the transfer of the product from the reservoir, for forming a drug delivery device, said adaptor comprising a collar engageable around said end-piece, and a foldable element capable of going from a folded configuration in which said foldable element substantially surrounds a distal portion of said end-piece, and an unfolded configuration, in which said foldable element leaves said distal portion at least partially uncovered, the foldable element provided with threaded portions forming a continuous thread when the foldable element is in its folded configuration.

* * * * *

UNITED STATES PATENT AND TRADEMARK OFFICE
CERTIFICATE OF CORRECTION

PATENT NO.        : 9,308,317 B2
APPLICATION NO.   : 14/232760
DATED             : April 12, 2016
INVENTOR(S)       : Gilbert Poncon Page 1 of 1

It is certified that error appears in the above-identified patent and that said Letters Patent is hereby corrected as shown below:

Claims

Column 9, Line 10, Claim 13, delete "device-according" and insert -- device according --

Column 9, Line 20, Claim 14, delete "in," and insert -- in --

Signed and Sealed this
Nineteenth Day of July, 2016

Michelle K. Lee
*Director of the United States Patent and Trademark Office*